United States Patent
Neirinckx

(10) Patent No.: US 7,015,199 B1
(45) Date of Patent: Mar. 21, 2006

(54) TREATMENT OF PSORIASIS THROUGH DOWN-REGULATION OF THE EGF-RECEPTOR WITH TOPICALLY-APPLIED EGF

(76) Inventor: Rudi D. Neirinckx, 3, Rue du Vignoble, Dietwiller (FR) 68440

( * ) Notice: Subject to any disclaimer, the term of this patent is extended or adjusted under 35 U.S.C. 154(b) by 364 days.

(21) Appl. No.: 09/584,978

(22) Filed: Jun. 2, 2000

(51) Int. Cl.
*A61K 31/505* (2006.01)
*A61K 38/18* (2006.01)

(52) U.S. Cl. ............................ 514/21; 514/12; 514/275

(58) Field of Classification Search ............... 514/2, 514/12, 21, 275; 530/324, 399; 544/297
See application file for complete search history.

(56) References Cited

U.S. PATENT DOCUMENTS 5,070,188 A * 12/1991 Njieha et al. ............... 530/324
5,130,298 A * 7/1992 Cini et al. ..................... 514/12
6,337,320 B1 * 1/2002 Hersh et al. ................... 514/18

FOREIGN PATENT DOCUMENTS

EP 0 339 905 A2 * 11/1989

OTHER PUBLICATIONS

Nanney et al. Modulation of Epidermal Growth Factor Receptors in Psoriatic Lesions During Treatment with Topical EGF. J. Invest. Dermatol. Mar. 1992, vol. 98, No. 3, pp. 296-301.*
Phan et al. Association Between Pyoderma Gangrenosum And Psoriasis. Lancet. Aug. 24, 1996. vol. 348, p. 547.*
Casaco et al. Topical Anti-Inflammatory Activity of Human Recombinant Epidermal Growth Factor. Skin Pharmacol. Appl. Skin Physiol. 1999. vol. 12, pp. 79-84.*

* cited by examiner

*Primary Examiner*—Jeffrey Edwin Russel
(74) *Attorney, Agent, or Firm*—Bell, Boyd & Lloyd LLC

(57) ABSTRACT

Topical agent formulations for the treatment of psoriasis containing epidermal growth factor (EGF) as the active agent. EGF precursors or biological equivalents can be used. The formulation can also contain an anti-inflammatory. The formulation can contain sulfadiazine.

2 Claims, No Drawings

TREATMENT OF PSORIASIS THROUGH DOWN-REGULATION OF THE EGF-RECEPTOR WITH TOPICALLY-APPLIED EGF

From unrelated but similar fields it is deduced that certain forms of psoriasis can be effectively treated through topical application of EGF-containing formulations. This patent application summarizes the theoretical basis for this finding and requests protection for the idea, while clinical evaluation is in preparation.

INTRODUCTION

Psoriasis is a chronic skin disorder that affects approximately 4.0 million people in the US., and annual treatment costs in the USA alone are estimated at over $1.5 billion. There are no currently available drugs for this disease that offer satisfactory efficacy and safety. Psoriatic lesions are caused by the hyperproliferation of keratinocytes, but it has been demonstrated that EGF-R signalling is required for the growth of keratinocytes.

The invention relates to methods for delivering, for example. EGF to a psoriatic site. Topical formulations or systemic administration can be used. The amount of EGF can range from 0.01 to 50 ug/g. The composition can contain 0.5–20 ug/q of EGF. The formulation also can contain other ingredients, such as an anti-inflammatory. The formulation can contain sulfadiazine. The amount of sulfadiazine can range from 0.1 to 3% (w/w) and the amount of EGF can range from 0.5–20 ug/g. For example, a formulation can contain 1% sulfadiazine and 10 $\mu$g of EGF.

EGF precursors, such as FGF, or molecules with similar function, such as urogastrone or EGF truncations can be used.

It has been demonstrated that the upper epidermal layer in psoriatic tissue contains levels of EGF-receptors (EGFR) more similar to the levels found in the mitotically-active basal cell layer of skin. In normal epidermis r-EGF is located primarily in the germinative layer, which contains r-EGF levels 4 times higher than those found in the more-diferentiated cells of the upper epidermal layers. In psoriatic lesions the upper epidermal layers shows r-EGF levels 2× higher than in normal tissue, while the germanitive layer has normal levels. (L. A. Nanney et al; *J. Invest. Dermat.* Vol 85, p 260–265).

There is only a poor correlation between the levels of r-EGF and the level of cellular proliferation. An example of cells with elevated metabolism but low mitotic activity is the case of the sweat duct epithelium. Similarly, the high level of r-EGF indicates elevated metabolism rather than lack of differentiation in psoriatic lesions.

PROPOSAL

As the main difference in r-EGF distribution in normal and psoriatic tissue is the abnormal retention of the receptor beyond the first 2–3 cell rows in the stratum basilis in psoriatic tissue, we propose to reduce these concentrations through a down regulation of the receptor using higher than normal levels of EGF at the level of the receptor.

This is similar to the down regulation of FSH and LH excretion through the saturation of pituitary GnRH receptors in response to a constant level f GnRH.

This down regulation is due to the deviation from the normal physiological situation where intermittent surges of GnRH release LH and FSH without causing saturation of the receptors. It is also similar to the effect of high levels of estradiol on estrogen-dependent tumour lines: In-vitro, the proliferation of these cells can be halted by high, non-physiological concentrations of the hormone.

It has been reported that high levels of EGF have inhibited the growth of EGF-dependent cancer cell lines in-vitro. The biological activity of epidermal growth factor (EGF) is mediated through the intrinsic tyrosine kinase activity of the EGF receptor (EGFR). In numerous cell types, binding of EGF to the EGFR stimulates the tyrosine kinase activity of the receptor eventually leading to cell proliferation. In tumor-derived cell lines, which overexpress the EGFR, however, growth inhibition is often seen in response to EGF. The mechanism for growth inhibition is unclear. A constant pressure of EGF may engender a similar down regulation of the EGF receptors and result in a more-normal metabolic activity and a reversion of psoriatic tissue to normal.

CLINICAL EVALUATION

Two patients, suffering from psoriasis, were treated with a topical cream containing sulfadiazine and 5 $\mu$g of EGF/gram of cream. The treatment was carried out by applying 2 grams of cream over each psoriatic lesion and was carried out twice a day for a week.

RESULTS AND CONCLUSION

After a week's treatment the psoriatic lesions showed—subjectively—a marked improvement, comparable to the result obtained after treatment with corticosteroids.

It is therefore felt that a larger clinical trial is warranted.

What is claimed is:

1. A method for treating psoriasis in a human patient in need thereof comprising the step of administering a topical formulation, wherein the formulation is a topical cream containing 0.1 to 3% (w/w) of sulfadiazine and 0.5 to 20 micrograms EGF/gram formulation.

2. The method according to claim 1, wherein the formulation comprises 10 $\mu$g EGF and 1% (w/w) sulfadiazine.

* * * * *